US00PP36133P3

(12) United States Plant Patent
Olesen

(10) Patent No.: US PP36,133 P3
(45) Date of Patent: Sep. 24, 2024

(54) ROSE PLANT NAMED 'POULCAS067'

(50) Latin Name: *Rosa hybrida*
Varietal Denomination: Poulcas067

(71) Applicant: Mogens Nyegaard Olesen, Fredensborg (DK)

(72) Inventor: Mogens Nyegaard Olesen, Fredensborg (DK)

(73) Assignee: Poulsen Roser, A/S, Fredensborg (DK)

( * ) Notice: Subject to any disclaimer, the term of this patent is extended or adjusted under 35 U.S.C. 154(b) by 141 days.

(21) Appl. No.: 17/803,633

(22) Filed: Sep. 13, 2022

(65) Prior Publication Data

US 2023/0140845 P1 May 4, 2023

(30) Foreign Application Priority Data

Sep. 24, 2021 (QZ) ..... PBR 2021/2366

(51) Int. Cl.
*A01H 5/02* (2018.01)
*A01H 6/74* (2018.01)

(52) U.S. Cl.
USPC ..... Plt./141
CPC ..... *A01H 6/749* (2018.05)

(58) Field of Classification Search
USPC ..... Plt./141
CPC ..... A01H 6/749; A01H 5/02
See application file for complete search history.

(56) References Cited

PUBLICATIONS

Poulsen Roser A/S (Year: 2023).*

* cited by examiner

*Primary Examiner* — Keith O. Robinson

(57) ABSTRACT

A new garden rose plant of the Compact Floribunda class which has abundant, pink flowers and attractive foliage. This new and distinct variety has shown to be uniform and stable in the resulting generations from asexual propagation.

2 Drawing Sheets

Botanical designation: *Rosa hybrida.*

Variety denomination: 'Poulcas067'.

This application claims priority to Plant Breeder's Rights Application Number 2021/2366, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Fredensborg, Denmark. The new variety, named 'Poulcas067', originated as a single seedling from the stated cross.

The new variety may be distinguished from its male pollen parent and female seed parent primarily by the following characteristics. The male pollen parent plant has a growth height of 25 cm and has white flowers while the new variety has pink flowers and grows to a height of 60 cm. The female seed parent plant has red flowers while the new variety has pink flowers.

The objective of the hybridization of this rose variety was to create a new and distinct variety with unique qualities, such as:

1. Uniform and abundant pink flowers;
2. Vigorous, but compact growth when propagated on its own roots; and
3. Exceptional disease resistance.

This combination of qualities is not present in previously available commercial cultivars of this type, known to the inventor, and distinguish 'Poulcas067' from all other varieties of which we are aware.

As part of the rose development program, Mogens N. Olesen germinated the seeds from the aforementioned hybridization during winter of 2012 and conducted evaluations on the resulting seedlings in a controlled environment in Fredensborg, Denmark. 'Poulcas067' was selected in the spring of 2013 by the inventor as a single plant from the progeny of the aforementioned hybridization.

Asexual reproduction of 'Poulcas067' by rooted cuttings was first done by Mogens N. Olesen in the nursery in Fredensborg, Denmark in July, 2013. This initial and other subsequent asexual propagations conducted in controlled environments have demonstrated that the characteristics of 'Poulcas067' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas067'.

Specifically illustrated in FIG. 1 of the drawings are open flowers viewed from above and the side, flower petals detached revealing reproductive flower parts, and sepals detached revealing the receptacle characteristics.

Figure 1:
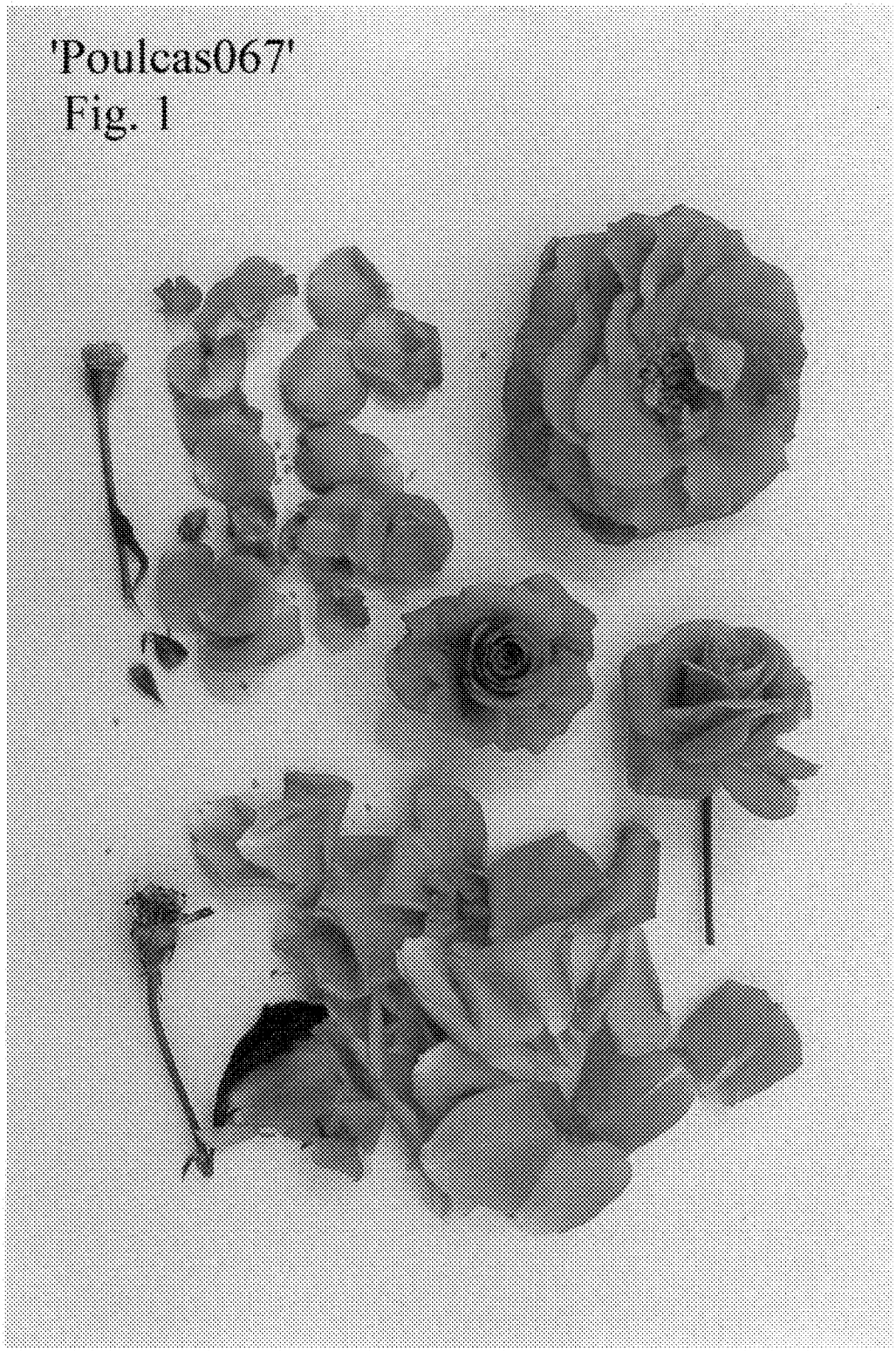
Figure 2:
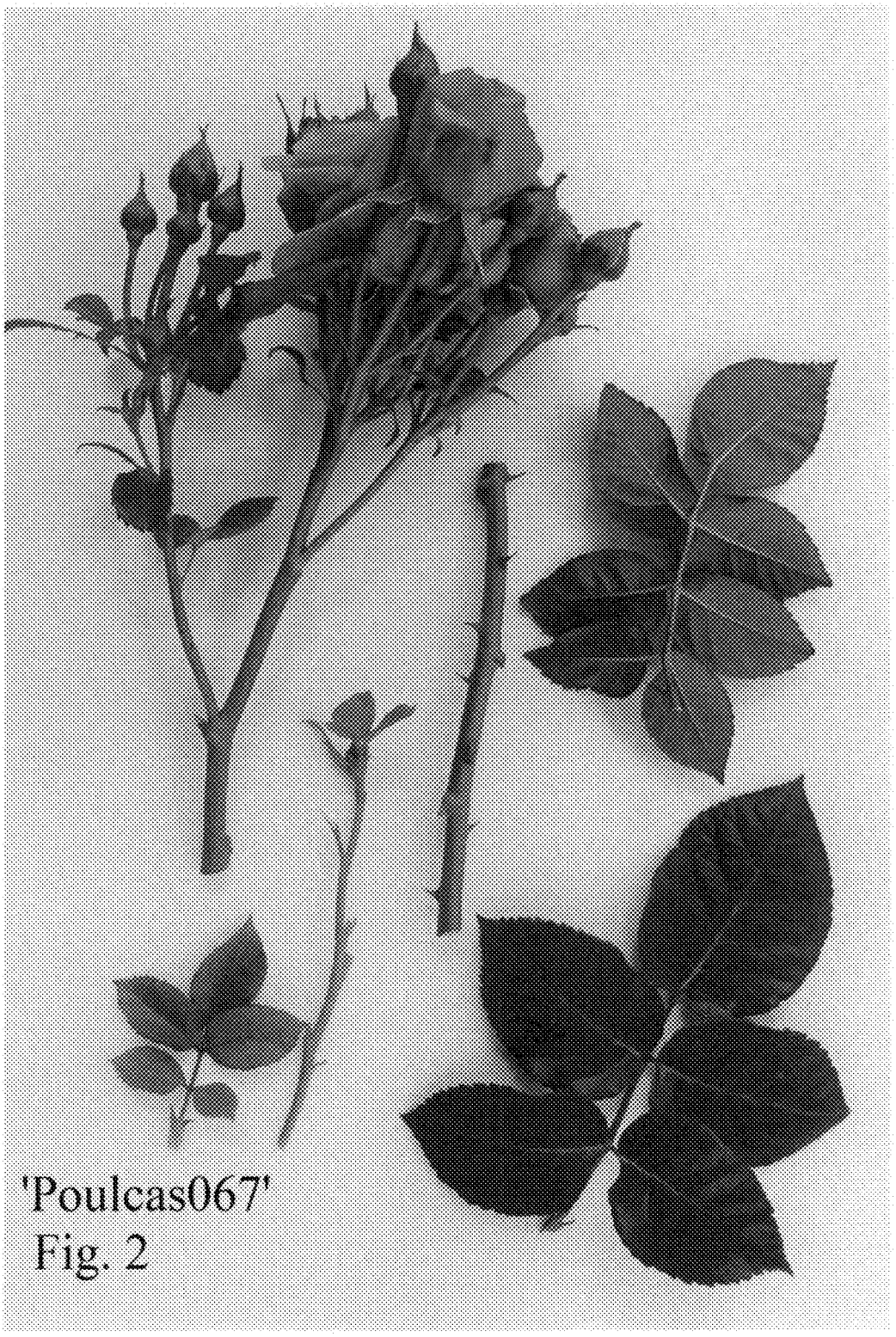

Specifically illustrated in FIG. 2 of the drawings are a cluster of flower buds and open flowers on a branch, juvenile leaves, juvenile stem, mature leaves, and mature stem showing prickles. Plants shown are 2 years of age.

DETAILED DESCRIPTION OF THE VARIETY

The following is a description of 'Poulcas067', as observed in its growth outdoor in Odense Denmark. Observed plants are 18 months of age, and were grown on their own roots in 30 cm containers. Color references are made using The Royal Horticultural Society (London, England) Colour Chart, 2001, except where common terms of color are used.

For a comparison, several physical characteristics of the rose variety 'Poulcas061', U.S. Plant Pat. No. 32,346 are compared to 'Poulcas067'.

General tonality of flower colour for 'Poulcas061' is Red-Purple Group 71B, while the claimed plant is Red-Purple Group N57A. 'Poulcas061' has a flower diameter of 80 mm, while the claimed plant 'Poulcas067' has flowers with a diameter of 100 to 105 mm. The claimed plant has strong rose perfume while 'Poulcas061' has moderate scent.

Flower and Flower Bud

Blooming habit: Continuous.

Flower bud:

- *Size.*—Upon opening, 25 mm in length from base of receptacle to end of bud. Bud diameter is 15 mm.
- *Bud form.*—Globose.
- *Bud color.*—As sepals divide petals are Red-Purple Group 60A.
- *Sepal inner surface.*—Color: Yellow-Green Group 146D. Surface: Lightly pubescent.
- *Sepal outer surface.*—Color: Yellow-Green Group 144A with light intonations of Greyed-Red Group 181A. Texture: Smooth.
- *Sepal shape.*—Apex: Cirrhose. Base: Flat at union with receptacle.
- *Sepal margin.*—Margins have weak foliaceous appendages on three of the five sepals.
- *Sepal size.*—25 mm long, 11 mm wide.
- *Receptacle.*—Texture: Smooth. Size: 7 mm in height, 8 mm wide. Color: Yellow-Green Group 144A. Shape: Campanulate.
- *Pedicel.*—Surface: Smooth. Length: 35 to 40 mm. Diameter: 3 mm on average. Color: Yellow-Green Group 144A. Strength: Strong.
- *Peduncle.*—Length: 15 to 80 mm. Diameter: About 4 mm. Color: Yellow-Green Group 144A. Texture: Smooth.

Flower bud development: Flower buds are borne in clusters in panicle form, of 15 to 20 flower buds per stem.

Flower bloom:

- *Fragrance.*—Strong rose perfume.
- *Duration.*—The blooms have a duration on the plant of approximately 14 days. Petals fall cleanly away from plant after flowers have fully matured.
- *Size.*—Fully opened, flower diameter is 100 to 105 mm when open. Flower depth is 30 to 40 mm.
- *Flower shape.*—Initially flowers are high centered, very double, with a tightly closed center. After full maturity flowers are button eye.
- *Shape of flower, side view.*—The upper portion is flat to flat convex. The lower portion is concave.

Petalage: Under normal conditions, flowers have about 35 petals.

General tonality of flower: Open flowers are Red-Purple Group N57A. After flowers have been open for one week, coloration becomes Red-Purple Group N57C.

Petal color:

- *Upon opening, outer petals.*—Upper surface: Red-Purple Group N57A with a small basal zone coloration of Yellow Group 2B. Lower surface: Red-Purple Group N57B with other intonations of Red-Purple Group N57C. Small Yellow Group 5B at the basal point of attachment.
- *Upon opening, inner petals.*—Upper surface: Red-Purple Group N57A. At the basal zone small Yellow Group 5A. Lower surface: Blend of Red-Purple Group 51B and Red Group 55A. At the basal zone, a small spot of Yellow Group 5C.
- *After opening, outer and inner petal.*—Upper surface: Red-Purple Group N57with a small spot of Yellow 4D at the basal point of attachment. Lower surface: Red-Purple Group N57C with a small petal spot Yellow Group 4D.

Petals:

- *Petal reflex.*—Slightly reflexed.
- *Margin.*—Several clefts in the margin with moderate undulations.
- *Shape.*—Broad and elliptic. Apex shape: Rounded. Base shape: Obtuse.
- *Size.*—50 mm (l)×60 mm (w).
- *Texture.*—Smooth on the upper and lower surface.
- *Thickness.*—Average.

Petaloids:

- *Size.*—20 mm (l) by 15 mm (w).
- *Quantity.*—About 8.
- *Shape.*—Rounded with a round base and rounded apex.
- *Margin.*—Strong undulations, entire.
- *Color.*—Upper Red-Purple Group N57A with a basal point of attachment Yellow Group 5A. The lower surface is Red-Purple Group 51B and Red Group 55A with a basal point of attachment Yellow Group 5C.

Reproductive flower parts:

- *Pollen.*—None observed.
- *Anthers.*—Size: 2 mm in length. Color: Yellow Group 5C and Yellow-Orange Group 17A. Quantity: 30 on average.
- *Filaments.*—Color: Yellow Group 9A and Orange-Red Group 33B. Length: 5 mm.
- *Pistils.*—Length: 5 mm. Quantity: 40 on average.
- *Stigmas.*—Color: Greyed-Yellow Group 160B.
- *Styles.*—Color: Green-White Group 157A.
- *Location of stigmas.*—Inferior in location relative to the length of the filaments and the height of the anthers.
- *Hips.*—None Observed.

Plant

Plant growth: Upright, bushy. Plants are 60 cm in height, and 65 cm wide.

Stems:

- *Color of juvenile growth.*—Yellow-Green Group 144A.
- *Color of mature growth.*—Yellow-Green Group 144A.

*Length.*—Canes are about 20 cm from the base of the plant to the flowering portion.

*Diameter.*—About 7 mm.

*Internodes.*—On mature canes about 45 mm between nodes.

*Surface texture.*—Young wood: Smooth. Older wood: Smooth.

Long prickles:

*Incidence.*—6 prickles per 10 cm of stem.

*Size.*—Average length of prickles on mature stems is 8 mm.

*Shape.*—Upper portion is linear. Lower portion is concave.

*Color.*—Juvenile prickles: Greyed-Purple Group 183B. Mature prickles: Greyed-Purple Group 183B.

Plant foliage:

*Compound leaf.*—180 mm (l)×155 (w).

*Quantity.*—2 leaves per 10 cm of stem on average.

*Leaf bearing angle to the stem.*—45 degrees.

*Color of juvenile foliage.*—Upper side: Yellow-Green Group 144A with intonations of Greyed-Purple Group 183A. Lower side: Yellow-Green Group 146C with intonations of Greyed-Purple Group 183A.

*Color of mature foliage.*—Upper side: Yellow-Green Group 147A. Lower side: Yellow-Green Group 147B.

Plant leaves and leaflets:

*Stipules.*—Size: 20 mm long, 3 mm wide. Quantity: 2 per compound leaf. Shape: Linear, slightly broad based with outward extending apices. Margins: Finely serrated. Color: Yellow-Green Group 144A.

*Petiole.*—Length: 32 mm. Diameter: 2 mm. Upper surface color: Yellow-Green Group 144A. Lower surface color: Yellow-Green Group 144A.

*Rachis.*—Length: 53 mm. Upper surface color: Yellow-Green Group 144A. Lower surface color: Yellow-Green Group 144A.

*Leaflet.*—Quantity: Normally 5 leaflets. Margins: Serrated. Size: Terminal leaflets are about 85 mm long, 60 mm wide. Shape: Generally elliptical. Base: Rounded. Apex: Acute. Texture: Smooth on upper surface, lower surface is rugose. Thickness: Average. Arrangement: Odd pinnate. Venation: Reticulate. Glossiness: Very glossy.

Disease resistance: Above average resistance to powdery mildew *Sphaerotheca pannosa* var. *rosae,* downy mildew *Peronospora sparsa,* rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulcas067' substantially as described and illustrated herein.

* * * * *

'Poulcas067'

'Poulcas067'